United States Patent [19]

Bundy

[11] 4,205,179

[45] May 27, 1980

[54] TRANS-2,3,13,14-TETRADEHYDRO-9-DEOXY-9-METHYLENE-PGF COMPOUNDS

[75] Inventor: Gordon L. Bundy, Portage, Mich.

[73] Assignee: The Upjohn Company, Kalamazoo, Mich.

[21] Appl. No.: 932,998

[22] Filed: Aug. 11, 1978

Related U.S. Application Data

[62] Division of Ser. No. 893,771, Apr. 5, 1978, Pat. No. 4,165,436.

[51] Int. Cl.² ............................................. C07C 177/00
[52] U.S. Cl. ...................................... 560/121; 260/408; 260/410; 260/410.5; 260/410.9 R; 260/413; 562/503
[58] Field of Search ........................ 560/121; 562/503; 260/410, 410.9 R, 413, 408

[56] References Cited

U.S. PATENT DOCUMENTS

| | | | |
|---|---|---|---|
| 4,028,350 | 7/1977 | Bundy | 260/240 |
| 4,138,590 | 2/1979 | Kao | 562/503 |

Primary Examiner—Robert Gerstl
Attorney, Agent, or Firm—Robert A. Armitage

[57] ABSTRACT

The present specification relates to novel 9-deoxy-9-methylene-trans-2,3-didehydro-PGF compounds with improved pharamcological properties. While these compounds are useful in inducing a wide variety of prostaglandin-like pharmacological effects, they are specifically useful as regulators of procreation and fertility.

14 Claims, No Drawings

TRANS-2,3,13,14-TETRADEHYDRO-9-DEOXY-9-METHYLENE-PGF COMPOUNDS

The present application is a divisional application of Ser. No. 893,771, filed 5 Apr. 1978, now U.S. Pat. No. 4,165,436, issued 21 Aug. 1979.

The present invention relates to prostaglandin analogs, for which the essential material contituting disclosure therefor is incorporated by reference here from U.S. Pat. No. 4,165,436.

I claim:

1. A prostaglandin analog of the formula

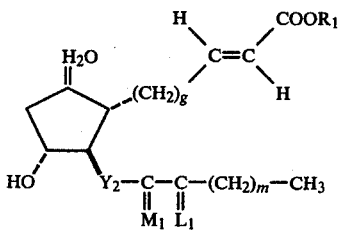

wherein m is one to 5, inclusive;
wherein $Y_2$ is $-C\equiv C-$;
wherein $M_1$ is

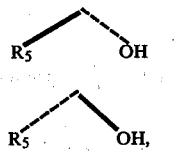

or

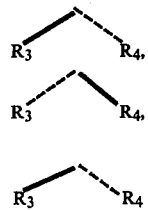

wherein $R_5$ is hydrogen or methyl;
wherein $L_1$ is

or a mixture of

and

wherein $R_3$ and $R_4$ are hydrogen, methyl, or fluoro, being the same or different, with the proviso that one of $R_3$ and $R_4$ is fluoro only when the other is hydrogen or fluoro;
wherein g is 4, 5, or 6;
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A prostaglandin analog according to claim 1, wherein m is 3.

3. A prostaglandin analog according to claim 2, wherein g is 4.

4. A prostaglandin analog according to claim 3, wherein at least one of $R_3$ and $R_4$ is fluoro.

5. 9-Deoxy-9-methylene-16,16-difluoro-trans-2,3,13,14-tetradehydro-PGF$_1$, a prostaglandin analog according to claim 4.

6. A prostaglandin analog according to claim 3, wherein at least one of $R_3$ and $R_4$ is methyl.

7. 9-Deoxy-9-methylene-16,16-dimethyl-trans-2,3,13,14-tetradehydro-PGF$_1$, a prostaglandin analog according to claim 6.

8. 9-Deoxy-9-methylene-16,16-dimethyl-trans-2,3,13,14-tetradehydro-PGF$_1$, methyl ester, a prostaglandin analog according to claim 6.

9. A prostaglandin analog according to claim 3, wherein $R_3$ and $R_4$ are both hydrogen.

10. A prostaglandin analog according to claim 9, wherein $R_5$ is methyl.

11. 9-Deoxy-9-methylene-15-methyl-trans-2,3,13,14-tetradehydro-PGF$_1$, a prostaglandin analog according to claim 10.

12. A prostaglandin analog according to claim 9, wherein $R_5$ is hydrogen.

13. 9-Deoxy-9-methylene-trans-2,3,13,14-tetradehydro-PGF$_1$, methyl ester, a prostaglandin analog according to claim 12.

14. 9-Deoxy-9-methylene-trans-2,3,13,14-tetradehydro-PGF$_1$, a prostaglandin analog according to claim 12.

* * * * *

UNITED STATES PATENT OFFICE
CERTIFICATE OF CORRECTION

Patent No. 4,205,179   Dated 27 May 1980

Inventor(s) Gordon L. Bundy

It is certified that error appears in the above-identified patent and that said Letters Patent are hereby corrected as shown below:

Column 1, lines 16-26, that portion of the formula reading

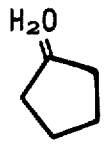    should read    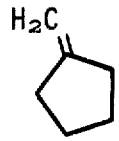

Signed and Sealed this

Fourteenth Day of *April 1981*

[SEAL]

Attest:

RENE D. TEGTMEYER

Attesting Officer   Acting Commissioner of Patents and Trademarks